United States Patent [19]

Pilling et al.

[11] Patent Number: 5,190,677
[45] Date of Patent: Mar. 2, 1993

[54] METHODS FOR PRODUCING STABILIZED SOLID THIOCARBONATE COMPOSITIONS

[75] Inventors: Richard L. Pilling; Donald C. Young, both of Fullerton, Calif.

[73] Assignee: Union Oil Comany of California, Los Angeles, Calif.

[21] Appl. No.: 738,870

[22] Filed: Aug. 1, 1991

Related U.S. Application Data

[60] Division of Ser. No. 290,992, Dec. 28, 1988, Pat. No. 5,039,327, which is a continuation-in-part of Ser. No. 253,139, Oct. 4, 1988, Pat. No. 4,908,143, and a continuation-in-part of Ser. No. 260,912, Oct. 21, 1988, Pat. No. 4,908,142.

[51] Int. Cl.$^5$ ............................................ C10M 135/14
[52] U.S. Cl. .................................. 252/17; 252/32.7 R; 252/33.6; 252/34; 252/38
[58] Field of Search .............................. 252/17, 33.6

[56] References Cited

U.S. PATENT DOCUMENTS

| | | | |
|---|---|---|---|
| 2,676,129 | 4/1954 | Bashour | 514/512 |
| 2,743,210 | 4/1956 | Tones et al. | 514/512 |
| 2,893,835 | 7/1959 | Stone et al. | 23/114 |
| 2,980,577 | 4/1961 | Neilsen | 514/512 |
| 3,023,142 | 2/1962 | Goodhue | 514/512 |
| 3,030,268 | 4/1962 | Margot | 514/512 |
| 3,074,844 | 1/1963 | Ogita | 514/512 |
| 3,180,790 | 4/1965 | Goodhue | 514/512 |
| 3,820,976 | 6/1974 | Wells et al. | 47/58 |
| 4,078,912 | 3/1978 | Hawkins | 71/28 |
| 4,198,782 | 4/1980 | Kydonieus et al. | 47/58 |
| 4,215,140 | 7/1980 | Otto et al. | 514/512 |
| 4,439,488 | 3/1984 | Trimnell et al. | 428/402.24 |
| 4,551,167 | 11/1985 | Young et al. | 47/58 |
| 4,726,144 | 2/1988 | Young et al. | 47/58 |
| 4,908,142 | 3/1990 | Dumdum et al. | 252/17 |
| 4,908,143 | 3/1990 | Dumdum et al. | 252/17 |
| 4,909,951 | 3/1990 | Mendelson et al. | 252/17 |
| 5,039,327 | 8/1991 | Pilling et al. | 71/27 |

OTHER PUBLICATIONS

Journal of the Chemical Society, vol. 89 (II), pp. 1812–1818 (1906), O'Donoghue and Kahan.
Journal of the Chemical Society, vol. 119, pp. 38–54 (1921), Yeoman.
Journal of the Chemical Society, vol. 128 (II), pp. 2326–2332 (1928), Mills and Robinson.
"Carbon Sulfides and Their Inorganic and Complex Chemistry," Gattow and Behrendt, Topics in Sulfur Chemistry, A. Senning, Editor, George Thieme Publishers, Stuttgart, pp. 173–177, (1977).

*Primary Examiner*—Ellen McAvoy
*Attorney, Agent, or Firm*—Charles L. Hartman; Gregory F. Wirzbicki

[57] ABSTRACT

Encapsulating particles of solid thiocarbonate salts, esters and complexes with air- and water-impermiable coatings produces compositions having long-term stability.

31 Claims, No Drawings

METHODS FOR PRODUCING STABILIZED SOLID THIOCARBONATE COMPOSITIONS

CROSS-REFERENCE TO RELATED APPLICATIONS

This application is a division of co-pending application Ser. No. 07/290,992 filed Dec. 28, 1988 now U.S. Pat. No. 5,039,327 which was a continuation-in-part of applications Ser. No. 253,139, filed Oct. 4, 1988 now U.S. Pat. No. 4,908,143 and U.S. Ser. No. 260,912, filed Oct. 21, 1988, now U.S. Pat. No. 4,908,142 both of which are herein incorporated by reference in their entireties.

BACKGROUND OF THE INVENTION

1. Field of the Invention

The present invention relates to stabilized solid thiocarbonate compositions and methods for producing same.

2. Background of the Invention

The chemistry of thiocarbonic acids and salts has been studied in some detail, as indicated by O'Donoghue and Kahan, Journal of the Chemical Society, Vol 89 (II), pages 1812-1818 (1906); Yeoman, Journal of the Chemical Society, Vol 119, pages 38-54 (1921); Mills and Robinson, Journal of the Chemical Society Vol. 128(II), pages 2236-2332 (1928) and by Stone et al in U.S. Pat. No. 2,893,835, dated Jul. 7, 1959.

According to O'Donoghue and Kahan, as far back as 1826 derivatives of thiocarbonic acid were prepared by Berzelius, who reacted aqueous solutions of hydrosulfides with carbon disulfide, the reactions occurring as in (1)

$$2KHS + CS_2 \rightarrow K_2CS_3 + H_2S \qquad (1)$$

giving unstable solutions which yielded unstable crystalline salts.

Other thiocarbonates were prepared and further characterized by O'Donoghue and Kahan. Their paper, at page 1818, reports the formation of ammonium thiocarbonate by reacting liquid ammonia with cold alcoholic thiocarbonic acid prepared by dropping a solution of "calcium thiocarbonate" into concentrated hydrochloric acid to produce free thiocarbonic acid ($H_2CS_3$). The "calcium thiocarbonate" utilized by the authors is described as a double salt, including the calcium cation in combination with both the hydroxide and the trithiocarbonate anions. In addition to making free thiocarbonic acid, other compounds prepared by O'Donoghue and Kahan included the sodium, potassium, zinc and lead salts. However, regardless of which of these salts were prepared, a common characteristic was their relative instability, with the prepared compounds breaking down and releasing carbon disulfide and hydrogen sulfide and/or a metal sulfide, often in a matter of minutes.

The noted paper by Yeoman reports a further study of thiocarbonates (called trithiocarbonates therein) and also reports the preparation and properties of perthiocarbonates (or tetrathiocarbonates) and derivatives of tetrathiocarbonic acid ($H_2CS_4$). Yeoman reports on methods of preparing the ammonium, alkali metal and alkaline earth metal salts of these acid species. For example, Yeoman prepared ammonium trithiocarbonate by saturating an alcoholic ammonia solution with hydrogen sulfide and then adding carbon disulfide to precipitate the product salt. Ammonium perthiocarbonate was prepared in a similar manner, except that after reacting the ammonia and hydrogen sulfide, elemental sulfur was added to form the disulfide, $(NH_4)_2S_2$; adding carbon disulfide immediately precipitated the product.

Yeoman states that "solutions of both ammonium trithiocarbonate and perthiocarbonate are very unstable" due to both decomposition to form thiocyanate as a product, and to "complete dissociation back into ammonia, hydrogen sulfide and carbon disulfide."

Considerable explanation is provided concerning the stability of thiocarbonates, as exemplified by sodium trithiocarbonate and perthiocarbonate. Sodium trithiocarbonate solutions in water are said to remain stable only if oxygen and carbon dioxide are "rigidly excluded"; the presence of oxygen causes decomposition to form carbon disulfide and thiosulfates, while carbon dioxide decomposes the solution to form a carbonate, elemental sulfur, carbon disulfide and hydrogen sulfide. Potassium trithiocarbonate behaves similarly, according to Yeoman.

Yeoman also attempted to prepare and characterize the stability of thiocarbonate salts of four of the alkaline earth metals. Yeoman was unable to prepare a "pure" calcium tri- or tetrathiocarbonate, but did observe that the double salt of calcium trithiocarbonate which he prepared was more stable (probably because it was less hygroscopic) than the sodium or potassium thiocarbonates. The barium tetrathiocarbonate could not be isolated, although Yeoman believed it existed in solution. Solid barium trithiocarbonate was found to be stable, although it was alleged to behave like sodium trithiocarbonate when dissolved in water. The preparation of aqueous solutions of the tri- and tetrathiocarbonate of magnesium and strontium was alleged, but the magnesium thiocarbonates were not isolated.

The previously noted paper by Mills and Robinson shows the preparation of ammonium thiocarbonate by digesting ammonium pentasulfide (obtained by suspending sulfur in aqueous ammonia, then saturating with hydrogen sulfide) with carbon disulfide. A crystalline residue from the reaction was found to be ammonium perthiocarbonate. The authors prepared a "better" ammonium perthiocarbonate product, however, by extracting the ammonium pentasulfide with carbon disulfide in a Soxhlet apparatus.

Stone et al disclose several methods for preparing solid ammonium, alkali and alkaline earth metal salts of tri- and "tetraperoxythiocarbonates," hereinafter referred to simply as "tetrathiocarbonates." One such method involves the solution of an active metal such as sodium in anhydrous ethanol to form an ethoxide which, in turn, is reacted with hydrogen sulfide and carbon disulfide to form sodium trithiocarbonate. They report, however, that the trithiocarbonates tend to be quite soluble in ethanol, and if it is desired to recover the solid material from the solution, it is necessary to treat the reaction mixture with a "displacing agent" such as ether, in which case the thiocarbonates frequently separate, not as solids, but as difficulty crystallizable oils which appear to be saturated aqueous solutions of the trithiocarbonate salt. Consequently, such a procedure is not considered feasible for use on a commercial scale. Similar problems were reported with tetrathiocarbonate salts, which were prepared by reacting a metal sulfide such as sodium sulfide with sulfur and carbon disulfide, using procedures analogous to those for the trithiocarbonates.

These problems were reportedly solved by carrying out the preparation reaction "in a medium which is composed of a major part of a nonsolvent for the reaction components and which contains only a minor proportion, less than sufficient to dissolve the inorganic sulfide, of a liquid which is miscible with said nonsolvent and which is a solvent, to a measurable degree, for the inorganic sulfides." For the reaction medium, the preferred nonsolvents comprise between about 70 and about 90 percent of one or more relatively low boiling hydrocarbon materials such as hexane, cyclohexane and benzene, with the second solvent preferably being between about 10 and about 30 percent ethanol, isopropanol or dioxane. Stone et al report that it is not necessary for the second solvent to be anhydrous and that the "usual" 95-5 commercial azeotrope of ethanol and water is quite satisfactory to produce hydrated salts such as $Na_2CS_3.3H_2O$, although the alcohol produces the aforementioned "oil" when used alone.

Basic physical and chemical properties of these materials and a number of basic method for making them are summarized in considerable detail, starting at page 154 of "Carbon Sulfides and their Inorganic and Complex Chemistry" by G. Gattow and W. Behrendt, Volume 2 of "Topics in Sulfur Chemistry" A. Senning, Editor, George Thieme Publishers, Stuttgart, 1977. However, regardless of which material is made and how it is produced, one common characteristic of the solid salts of tri- and tetrathiocarbonic acid is their relatively poor long term stability and many tri- and tetrathiocarbonate salts will decompose and release carbon disulfide upon exposure to water or air, often within a few hours or even minutes. This is not necessarily bad, if one wishes to use the released $CS_2$ as a soil fumigant and nematicide. However, where it is desired to provide solid materials for such uses as lubrication or rubber additives, or "dry land" farming, etc., it is necessary that they be produced in one or more forms which provide for and maintain the long term stability of these salts when so used. As disclosed in copending U.S. patent application Ser. Nos. 253,139 and 260,912, one method of stabilizing these salts is to coat the solid particles with an oil or grease. Another is to prepare the salts under completely anhydrous conditions and then store the resultant materials under a dry, inert gas such as argon, hydrogen or, preferably, nitrogen until they are put into use. What is needed are improved methods to prevent their decomposition under ambient conditions. The present invention provides such methods.

SUMMARY OF THE INVENTION

In its broadest aspects, the present invention comprises stabilized solid particles of one or more salts, thioesters or complexes of a thiocarbonate and a method for making same. The thiocarbonate species used are those which show short or long term degradation in the presence of water, $CO_2$ or $O_2$ and said method comprises first putting said particles into a condition in which they are presently substantially free of water, $CO_2$ and $O_2$ and then encapsulating them in a coating to protect them from future contact with air and water. Preferably the method comprises the steps of:

(1) forming said particles in a medium in which said thiocarbonate is stable and substantially insoluble;

(2) separating said particles from said medium so that said particles are substantially water-free and in an environment which is substantially free of water, $CO_2$ and $O_2$; and (3) encapsulating said particles with a coating to protect them from future contact with air and water.

As used herein, the term "water-free," when applied both to the stabilized solids of the present invention and to the media in which said stabilized solids are prepared, shall mean that the water content thereof is below the amount which would cause observable decomposition or hydrolysis of an unprotected thiocarbonate which is dissolved or suspended therein or which results in the formation and separation of an aqueous solution of said solids. Also, as used herein, the term "thiocarbonate" shall mean those compounds containing a group of the general formula:

$$(C_aS_b)$$

wherein a is between about 1 and about 4 and b is between about 3 and about 9 and $(C_aS_b)$ is present as the anionic moiety in a salt, as the acidic moiety of a thioester, or as a ligand in a metallic complex. The term "complex" shall refer to any compound in which $(C_aS_b)$ acts as a complexing ligand.

DETAILED DESCRIPTION OF THE INVENTION

The present invention comprises stabilized solid thiocarbonate salts, thioesters and complexes, and methods for making same. The salts and thioesters of this invention have the general formula $M_c(C_aS_b)_y$ wherein a, the number of carbon atoms therein, ranges between about 1 and about 4, preferably between about 1 and about 3, and more preferably is 1, b, the number of sulfur atoms therein, ranges between about 3 and about 9, preferably between about 3 and about 6, and more preferably is 3 or 4, M is hydrogen, a cationic salt-forming moiety or an organic thioester forming radical, y is the valence of M and c is the valence of $(C_aS_b)$.

A first embodiment of the present invention is directed to a method for making and storing stable salts and thioesters of tri- and tetrathiocarbonic acid. Although hydrogen sulfide and carbon disulfide would be expected to react to form trithiocarbonic acid according to the reaction:

$$H_2S + CS_2 \rightarrow H_2CS_3 \quad (2)$$

such is not the case. Consequently, other approaches to making derivatives of the thiocarbonic acids must be used. One method for making alkaline earth and heavy metal salts is by reacting a suitable salt, such as the acetate, with a stable solution of an ammonium thiocarbonate, such as that prepared by the procedure of Example 1 in U.S. Pat. No. 4,726,144, the teachings of which are incorporated herein in their entirety, by reference, to precipitate an insoluble salt product.

Solid trithiocarbonate salts and thioesters useful for the purposes of the present invention are preferably prepared by reacting a mixture, preferably a stoichiometric mixture, of carbon disulfide and a source of sulfide of the form $M_2S_y$, wherein M is a positive salt-forming moiety or the organic moiety of a mercaptan and y is the valence of M, said reaction being performed under conditions sufficient to produce a trithiocarbonate salt or thioester according to the general reaction:

$$M_2S_y + y\ CS_2 \rightarrow M_2(CS_3)_y \quad (3)$$

This reaction may be carried out at any temperature from 0° C. to the boiling point of carbon disulfide, and preferably from about 15° C. to about 35° C. The reaction is preferably carried out under an inert or reducing gas atmosphere to avoid oxidation of any of the sulfur compounds to sulfur oxide moieties such as thiosulfate.

Suitable cationic salt-forming moieties for M are ammonium, quaternary ammonium, quaternary phosphonium, quaternary arsonium, metals and metal complexes formed with commonly known ligands such as ammonia, ethylenediamine, diethylenetriamine, propylenediamine and pyridine. Preferably these moieties are ammonium or metals, more preferably alkaline earth or alkali metals, most preferably ammonium, sodium or potassium, and very most preferably potassium.

Suitable thioester forming organic moieties for M are alkyl, cycloalkyl, aryl, arylalkyl or alkylaryl groups, preferably alkyl groups having from 1 to about 8 carbon atoms, more preferably alkyl groups having 1 to about 5 carbon atoms, and most preferably alkyl groups having between 1 and about 3 carbon atoms.

The presence of significant amounts of water in the reaction vessel often tends to cause the formation of pasty, crusty, oil-like salt deposits therein, which are removable only with the greatest difficulty. Moreover, even for thiocarbonate species which are nominally insoluble in water, long-term exposure to water will often cause some degree of degradation. Consequently, the above reaction preferably takes place in a water-free liquid medium, which, while being a solvent for the source of sulfide, does not dissolve, to any great extent, the thiocarbonate salt or ester formed by this reaction, thus allowing it to precipitate out for subsequent recovery.

While any "water-free" solvent for the source of sulfide may be used, the preferred solvents in which to perform this reaction are the lower molecular weight, saturated absolute alcohols such as methanol, ethanol, propanol, isopropanol, n-butanol, isobutanol and secondary butanol. Such alcohols offer the advantages of (1) being commercially available in a water-free, absolute condition at low cost, (2) being miscible with carbon disulfide, and (3) being relatively good solvents for the metal sulfides, mercaptans and acetates used. The particular alcohol used depends on the particular end-product desired. For example, where the end-product is an alkali metal trithiocarbonate, particularly sodium and potassium trithiocarbonate, the relatively high solubility of these salts in methanol and ethanol would dictate that an alcohol wherein said salt is much less soluble such as isopropanol or, preferably, n-butanol be used.

Where an alcohol is used as the water-free solvent, one convenient way of forming the source of sulfide is the reaction of hydrogen sulfide with a metal alkoxide of the form $M(OA)_y$, wherein A is an alkyl radical and y is the valence of M. This alkoxide is generated in-situ either by dissolving a reactive metal, preferably an alkali or an alkaline earth metal, more preferably an alkali metal, most preferably sodium or potassium, and, very most preferably, potassium, or a reactive hydroxide, preferably an alkali metal hydroxide, most preferably sodium or potassium and, very most preferably, potassium hydroxide, in the alcohol according to the reactions:

$$2K + 2AOH \rightarrow 2KOA + H_2 \quad (4)$$

or, preferably, by:

$$KOH + AOH \rightarrow KOA + H_2O \quad (5)$$

Because of the aforementioned sensitivity of the potassium thiocarbonates to the presence of water, it is necessary that the water generated in reaction (5) be removed prior to any further processing. One approach for so doing is to heat the solution to a temperature high enough for an alcohol-water azeotrope to form and boil off. Another approach is to pass the solution through an absorbent, such as a molecular sieve, which is useful for separating out the water.

After the water is removed, passing hydrogen sufide through the remaining solution will convert the alkoxide to said source of sulfur, after which the addition of carbon disulfide, as shown in equation (3) above, will complete the reaction. Where the cationic salt-forming moiety is to be an alkaline earth or a heavy metal such as iron, copper, nickel, zinc, lead, or cadmium, such a salt can be made by reacting the potassium thiocarbonate salt, as just formed in the water-free medium, with an alcohol soluble salt such as the acetate of the moiety, which is subsequently added thereto. To do this, alcohols such as methanol and ethanol, which are capable of dissolving substantially all of both the alkali metal trithiocarbonate and the heavy metal acetate, are preferred.

The stable tetrathiocarbonate salts and thioesters of this invention are prepared in a similar manner, with the general reaction defined in equation (3) above being:

$$y\,S + M_2S_y + y\,CS_2 \rightarrow M_2(CS_4)_y \quad (6)$$

A second preferred embodiment of the present invention is the formation of one or more stabilized thiocarbonate complexes of the form:

$$(CI)_x(M_z(C_aS_b)_y)$$

wherein M is a cationic complex-forming metal such as tin, lead, or a transition metal such as iron, cobalt, nickel, platinum, copper, zinc, cadmium, mercury, chromium, manganese, molybdenum, etc., CI is a neutralizing counter ion such as quaternary ammonium, quaternary arsonium, quaternary phosphonium or quaternary stibonium, a is the number of carbon atoms in the complex, ranging between 1 and about 4, b is the number of sulfur atoms in the complex, ranging between about 3 and about 9, x is the number of counter ions necessary to neutralize the complex, y is the number of thiocarbonate groups in the complex and z is the number of cationic complex forming moieties in the complex.

One method for the preparation of such complexes is by reacting a mixture of an alkali metal thiocarbonate, prepared as described above, with a soluble complex forming moiety and a soluble cationic counter ion, preferably one containing quaternary ionic groups of the form:

$$(R_2 - \underset{\underset{R_4}{|}}{\overset{\overset{R_1}{|}}{Q}} - R_3)^+$$

with Q being nitrogen, arsenic, antimony or phosphorus, and with each R group being separately and independently hydrogen or, preferably an organic radical, said organic radical preferably being an alkyl, aryl, cycloalkyl or alkylaryl group having up to about 50 carbon atoms. It is understood that other cationic counter ionic moieties such as alkali and alkaline earth metals may be substituted for the quaternary moieties, for example, by ion exchange techniques.

The invention comprises the preparation and use of still other stabilized thiocarbonate compositions. Among the thiocarbonates suitable for this purpose are the metal salts of organic radical substituted thioesters such as potassium methyl trithiocarbonate, alkyl dimers having the forms $(MCS_3)_2$ and $(MCS_4)_2$, and salts and esters of the general form $M_2(C_3S_5)_y$, wherein y is the valence of M, as well as complexes made therewith. Still other solid carbon-sulfur compounds within the broad definition given above and methods for synthesizing them can be found in any advanced treatise on carbon-sulfur chemistry. Where such compounds prove to be sensitive to water, $CO_2$ or $O_2$, they too can be stabilized by the method of the present invention.

The second step in the preparation of the stabilized solid compositions of the present invention is the separation of the precipitated salt, thioester or complex product from the reaction medium. There are a number of methods suitable for such separation, including filtration and centrifuging. Whichever is used, the major factors of concern are the removal of any water in the medium so that at the conclusion thereof the particles are substantially water-free, and in an environment which is substantially free of degradative media such as oxygen, carbon dioxide and/or water. Once separated, any residual reactants can be removed with one or more washings with an inert solvent miscible with alcohol and carbon disulfide, such as pentane, hexane, and ether, either alone or in a mixture with fresh alcohol. Since it avoids the introduction of other, foreign materials into the process, a mixture of fresh alcohol and carbon disulfide is preferred. Where the separated particles were prepared in a water-containing medium, absolute ethanol in particular, offers the advantage of being miscible with water and, therefore, readily removing it.

The washed product may be dried to form freely flowing particles at moderate temperatures, either under vacuum or under a flowing stream of an inert gas such as argon, hydrogen or, preferably nitrogen. Once separated and dried, the solid product may be safely stored in opaque, sealed containers, preferably under a dry nitrogen atmosphere.

For an application, such as agricultural use in irrigated fields, such protective storage is quite adequate to keep the solids in proper condition until they are needed. However, there are many others where the particles must either survive for long periods of time, either in the open air or in contact with water, or decompose, in a controlled manner, over some period of time. Such uses include anti-wear/extreme pressure additives for petroleum base lubricants and, particularly water emulsified cutting oils. Another use is as a general agricultural pesticide in non-irrigated areas. In these and other situations where contact with air or water is expected, the solid particles must be coated with one or more materials capable of either preventing contact of the solid particles with the surrounding environment or controlling the degree to which such contact shall occur.

There are a number of final coating methods which can be used, depending upon the particular needs being addressed. For example, for agricultural use, the particles may be coated with a biodegradable coating such as a wax which may be applied either by contacting the particles with a wax solution in a low boiling hydrocarbon solvent, and then heating the mixture to drive off the solvent, or by contacting the particles with the molten wax under conditions adapted to keep the protected salt or complex in particulate form. Upon depositing the thus coated solids in the soil, the wax coating could be removed either by natural weathering or by attack by soil bacteria and other organisms, with the result that, over time, the particles would be exposed to the environment and decompose to form a soil pesticide.

Where longer term survival in agricultural use is desired, the particles may be encapsulated with sulfur, again either by being contacted by a sulfur solution in carbon disulfide or with molten sulfur. Such an application would be highly advantageous since sulfur is also widely used for pH control and other soil conditioning purposes, so a single application of particles so coated would serve two purposes—soil conditioning and long term pest control. Experience has shown that sulfur coatings tend to be brittle and will, on occasion, crack, thus exposing the coated particles to outside air and moisture. Where such cracking has been observed, it is found that applying a second coating of petrolatum to the particles will fill the cracks with an air-tight material, which, like the sulfur, is readily biodegradeable.

Where the particles are to be used as an extreme pressure/anti-wear additive, other approaches can be used. For machine oils and greases, merely coating the particles with a water-free oil or grease will usually serve to keep thiocarbonate salts and complexes from decomposing. Where the particles are to be used as extreme pressure additives in water-containing media such as emulsified cutting oils, other approaches must be used. Preferably, such coatings are polymerizable monomers, such as methyl methacrylate, or polymerizable natural oils such as linseed or tung oil. These polymers will form sturdy water and air tight coatings which will protect the encapsulated particles until they are crushed beneath the tool tip at the point of extreme-pressure contact. In such using, it is preferred that the polymer be substantially non-biodegradable.

The invention will be further described with reference to the following examples which are provided to illustrate and not limit the present invention.

EXAMPLE 1

Twenty grams (0.36 moles) of reagent grade potassium hydroxide was added to 200 grams (255 cc) of absolute ethyl alcohol, with the mixture being refluxed until all of the KOH had dissolved (approximately 1 hour), after which the water formed was removed by a conventional water-alcohol azeotropic distillation. After adding a sufficient amount of absolute alcohol to bring the alcoholic solution back up to about 250 cc and cooling the solution back to room temperature, 5.7 grams (0.18 moles) of finely divided sulfur was added, with stirring, after which 6.1 grams (0.18 moles) of hydrogen sulfide was dissolved therein. At the conclusion of this addition, the temperature of the exothermically heated solution was adjusted to about 130° F. and 13.6 grams (0.19 moles) of carbon disulfide were added, dropwise, thereto over a period of about 30 minutes. The mixture was then heated, under reflux, with stirring, for between about 20 minutes and about 1 hour, after which time a yellow-orange precipitate of potassium tetrathiocarbonate formed. The precipitate was vacuum filtered, under an inert atmosphere, and washed 3 times with about 50 cc of pentane. The washed material was dried, under vacuum, for about 8 hours at 60° C., to produce free-flowing salt particles.

EXAMPLE 2

Nine grams of zinc sulfate monohydrate (0.05 moles) and 45 grams of benzyl triphenyl phosphonium chloride (0.107 moles) were dissolved in 1200 cc of deionized water. After filtration to remove a small amount of insoluble material there was added, at room temperature and with stirring, 300 cc of an aqueous solution containing 0.51 moles of sodium tetrathiocarbonate prepared as described in U.S. Pat. No. 4,726,144. A yellow precipitate formed which after being separated by filtration was washed with water, ethanol and ether. After drying in a desiccator, the free-flowing complex particles had a melting point of 145° to 152° C. A comparison of the elemental analysis of the solid and for one having the theoretical composition of $((C_6H_5)_3C_6H_5CH_2P)_2(CS_4)_2Zn$ is as follows:

|  | Actual wt. % | Theoretical wt. % |
| --- | --- | --- |
| phosphorus | 5.9 | 5.88 |
| carbon | 59.6 | 59.32 |
| hydrogen | 4.1 | 4.22 |
| sulfur | 22.3 | 24.36 |
| zinc | 5.9 | 6.21 |

EXAMPLE 3

Twenty grams (0.36 moles) of reagent grade potassium hydroxide was added to 200 grams (255 cc) of absolute ethyl alcohol, with the mixture being refluxed until all of the KOH had dissolved, after which the water formed was removed by a conventional water-alcohol azeotropic distillation. After adding a sufficient amount of absolute alcohol to bring the alcoholic solution back up to about 250 cc, and cooling the solution back to room temperature, 7.4 grams (0.22 moles) of hydrogen sulfide was added with vigorous stirring, followed by 13.6 grams (0.19 moles) of carbon disulfide, which was added through a dropping funnel. The mixture was then stirred, at room temperature, for about 90 minutes during which time a light yellow precipitate of potassium trithiocarbonate formed. The precipitate was vacuum filtered, under an inert atmosphere, and washed 3 times each with ethanol and ether. The washed material was dried, under vacuum, for about 8 hours at 60° C., to produce free-flowing salt particles.

EXAMPLE 4

47.5 grams of commercial paraffin wax was brought to a temperature about 10° F. above its melting point at which time 47.5 grams of the potassium tetrathiocarbonate, as prepared in Example 1, and 5 grams of a commercial surfactant were added. The mixture was stirred for about 10 minutes at 5,000 RPM using a Cowles disperser. The hot liquid suspension was poured onto release paper on a cold slab and was allowed to cool. The resulting block had good stability and there was only a faint odor of $CS_2$.

EXAMPLE 5

38 grams of the potassium tetrathiocarbonate, as prepared in Example 1, were mixed with 53 grams of heavy mineral oil and 9 grams of a surfactant which was soluble therein for about 10 minutes at 5,000 RPM using a Cowles disperser. While there was slow settling of the initially uniform suspension, the material could be readily redispersed with only mild agitation. There was a slow loss of $CS_2$ from the suspension as compared with a rapid degradation and loss of $CS_2$ from the solid unprotected potassium tetrathiocarbonate when it was exposed to the atmosphere.

EXAMPLE 6

Potassium methyl trithicarbonate ($K(CH_3CS_3)$) was prepared by combining 2532 g (33.3 mole) of carbon disulfide, which had previously been chilled to $-5°$ C., with 265 g (4.0 mole) of 85% potassium hydroxide with stirring under a nitrogen atmosphere. Following the addition of the KOH, 230 g (4.8 mole) of methyl mercaptan was added, dropwise, over a period of about 4 hours, during which time the mixture was stirred and maintained at a temperature of about 2° C., after which the mixture was stirred, under nitrogen for an additional 16 hours. At the conclusion of this time about 3 liters of ether were added and the mixture stirred for an additional 24 hours, during which time a yellowish colored solid material precipitated out. This was separated from the ether/$CS_2$ mixture by vacuum filtration and dried, under vacuum for a period of about 4 days. The yield was about 543 g of a material having the following analysis:

| ($K(CH_3CS_3)$) | Actual wt. % | Theoretical wt. % |
| --- | --- | --- |
| carbon | 15.1 | 14.8 |
| hydrogen | 2.0 | 1.9 |

To about 150 cc of absolute ethanol, with about 16.2 grams of the potassium methyl trithiocarbonate, synthesized above, dissolved therein, was added about 12.7 grams of iodine dissolved in an additional 150 cc of absolute ethanol. The iodine solution was added dropwise at ambient temperature with continuous stirring. At the conclusion of this addition, the reaction mixture was poured into about 1000 cc of cool water, as a result of which a light yellow solid formed and precipitated. This was filtered off and dried under reduced pressure. About 7.5 grams of solid was obtained with a melting point of 88°-89° C. A comparison of the elemental analysis of the solid and one having the theoretical composition $(CH_3CS_3)_2$ is as follows:

|  | Actual wt. % | Theoretical wt. % |
| --- | --- | --- |
| carbon | 18.5 | 19.5 |
| hydrogen | 3.2 | 2.4 |
| sulfur | 74.0 | 78.0 |

Obviously many modifications and variations of this invention, as herein above set forth, may be made without departing from the spirit and scope thereof, and therefore only such limitations should be imposed as are indicated in the following claims. All embodiments which come within the scope and equivalency of the claims are, therefore, intended to be embraced therein.

We claim:

1. A method for making stabilized solid particles of a thiocarbonate selected from the group consisting of alkali and alkaline earth metal tri- and tetrathiocarbonates, and combinations thereof, said method comprising the steps of:
   (1) forming particles of a thiocarbonate selected from alkali and alkaline earth metal tri- and tetrathiocarbonates generally unstable in soil in a water-free medium in which said thiocarbonate is stable and substantially insoluble;
   (2) separating said particles from said medium so that said particles are substantially water-free and in an environment which is substantially free of water, $CO_2$ and $O_2$; and
   (3) dispersing said particles in a matrix selected from the group consisting of water-resistant wax, oil, grease, and combinations thereof in an amount sufficient to increase the stability of said thiocarbonate in soil.

2. The method of claim 1 wherein said thiocarbonate is of the form:

$$M_c(C_aS_b)_y$$

wherein M is a cationic salt forming moiety, a ranges between 1 and about 4, b ranges between about 3 and about 9, c is the valence of ($C_aS_b$) and y is the valence of M 3. The method of claim 2 wherein a ranges between 1 and 3, b ranges between 3 and 5, and c is 1 or 2.

4. The method of claim 2 wherein a is 1, b is 3 or 4 and c is 2.

5. The method of claim 4 wherein M is a cationic salt-forming moiety selected from the group consisting of ammonium, quaternary ammonium, quaternary phosphonium, quaternary arsonium, metals and metal complexes formed with ammonia, ethylenediamine, diethylenetriamine, propylenediamine and pyridine.

6. The method of claim 4 wherein M is selected from the group consisting of ammonium, alkaline earth metals and alkali metals.

7. The method of claim 2 wherein M is an alkali metal.

8. The method of claim 2 wherein M is alkali metal.

9. The method of claim 7, wherein said alkali metal is selected from sodium, potassium, and combinations thereof.

10. The method of claim 1 wherein said thiocarbonate salt comprises the reaction product of carbon disulfide and a source of sulfide of the form $M_2S_y$, wherein M is a cationic salt-forming moiety, and y is the valence of M, said reaction being performed in a liquid water-free medium under conditions sufficient to produce a trithiocarbonate salt of the general form $M_2(CS_3)_y$.

11. The method of claim 10 wherein said liquid water-free medium is selected from the group consisting of methanol, ethanol, propanol, isopropanol, n-butanol, isobutanol and secondary butanol.

12. The method of claim 10 wherein said source of sulfide is produced by the steps of:
   a) reacting an alkali metal hydroxide with a water-free alcohol selected from the group consisting of methanol, ethanol, propanol, isopropanol, n-butanol, isobutanol and secondary butanol, to form a solution of an alkoxide of the form, MOA, wherein M is an alkali metal radical and A is an alkyl group; and
   reacting said alkoxide with hydrogen sulfide to form said source of sulfide.

13. The method of claim 1 wherein said thiocarbonate salt comprises the reaction product of a source of sulfide of the form $M_2S_y$, wherein M is a cationic saltforming moiety, and y is the valence of M, with a mixture of elemental sulfur and carbon disulfide, said reaction being performed in a liquid water-free medium under conditions sufficient to produce a tetrathiocarbonate salt of the general form $M_2(CS_4)_y$.

14. The method of claim 13 wherein said liquid water-free medium is selected from the group consisting of methanol, ethanol, propanol, isopropanol, n-butanol, isobutanol and secondary butanol.

15. The method of claim 13 wherein the source of sulfur, elemental sulfur and carbon disulfide are present in a stoichiometric mixture for the general reaction:

$$M_2S_y + yS + yCS_2 = > M_2(CS_4)_y$$

16. The method defined in claim 1, wherein, in step (3), said thiocarbonate particles are dispersed in a water-resistant wax.

17. A method for making stabilized solid particles of a thiocarbonate salt of the form:

$$M_2(CS_b)_y$$

wherein M is selected from the group consisting of alkali metals, alkaline earth metals, and combinations thereof, b is an integer between about 3 and about 5, and y is the valance of M, said salt being generally unstable in soil, said method comprising the steps of:
   (1) forming said particles in a water-free liquid medium in which said thiocarbonate salt is substantially insoluble;
   (2) separating said particles from said medium so that said particles are substantially water-free and in an environment which is substantially free of water; $CO_2$ and $O_2$; and
   (3) dispersing said particles in a matrix selected from the group consisting of water resistant wax, oil, grease, and combinations thereof the relative proportions of said thiocarbonate salt and said matrix being sufficient to provide sufficient thiocarbonate to fumigate soil and sufficient matrix to reduce the rate of decomposition of said thiocarbonate salt when said particles are applied to soil.

18. The method of claim 17 wherein b is 3 and step (1) comprises the steps of:
   a) reacting an alkali metal hydroxide with a water-free alcohol selected from the group consisting of methanol, ethanol, propanol, isopropanol, n-butanol, isobutanol and secondary butanol, to form a solution of an alkoxide of the form, MOA, wherein M is an alkali metal radical and A is an alkyl group;
   b) reacting said alkoxide with hydrogen sulfide to form a source of sulfide; and
   c) reacting said source of sulfide with carbon disulfide to form an alkali trithiocarbonate salt.

19. The method of claim 17 wherein b is 4 and step (1) comprises the steps of:
   a) reacting an alkali metal hydroxide with a water-free alcohol selected from the group consisting of methanol, ethanol, propanol, isopropanol, n- butanol, isobutanol and secondary butanol, to form a solution of an alkoxide of the form, MOA, wherein M is an alkali metal radical and A is an alkyl group;

b) reacting said alkoxide with hydrogen sulfide to form a source of sulfide and c) reacting said source of sulfide with a mixture of sulfur and carbon disulfide to form an alkali tetrathiocarbonate salt.

20. The method defined in claim 17, wherein M is alkali metal, b is 3 or 4, or a value between 3 and 4, and y is 1.

21. The method defined in claim 20, wherein said alkali metal is selected from sodium, potassium, and combinations thereof.

22. The method defined in claim 20, wherein said thiocarbonate salt comprises a tetrathiocarbonate.

23. The method defined in claim 17, wherein M is an alkaline earth metal, b is 3 or 4, or a value between 3 and 4, and y is 2.

24. The method defined in claim 17, wherein, in step (3), said thiocarbonate particles are dispersed in a water-resistant wax.

25. A method for making stabilized solid particles of a tetrathiocarbonate salt generally unstable in soil, of the form:

$$M_2(CS_4)_y$$

wherein M is a cationic salt forming moiety, and y is the valence of M, said method comprising the steps of:

(1) forming said particles in a water-free liquid medium in which said thiocarbonate salt is substantially insoluble;

(2) separating said particles from said medium so that said particles are substantially water-free and in an environment which is substantially free of water, $CO_2$ and $O_2$; and (3) dispersing said particles in a matrix selected from the group consisting of water resistant wax, oil, grease, and combinations thereof the relative proportions of said thiocarbonate salt and said matrix being sufficient to completely encompass said thiocarbonate salt within said matrix and substantially increase the stability of said thiocarbonate salt when said particles are applied to soil.

26. The method of claim 25 wherein step (1) comprises the steps of:

a) reacting an alkali metal hydroxide with a water-free alcohol selected from the group consisting of methanol, ethanol, propanol, isopropanol, n-butanol, isobutanol and secondary butanol, to form a solution of an alkoxide of the form, MOA, wherein M is an alkali metal radical and A is an alkyl group;

b) reacting said alkoxide with hydrogen sulfide to form said source of sulfide; and c) reacting said source of sulfide with a stoichiometric amount of sulfur and carbon disulfide for the general reaction:

$$M_2S_y + yS + yCS_2 = > M_2(CS_4)_y.$$

27. The method defined in claim 25, wherein M is an alkali metal, b is 3 or 4, or a value between 3 and 4, and y is 1.

28. The method defined in claim 27, wherein said alkali metal is selected from sodium, potassium, and combinations thereof.

29. The method defined in claim 28, wherein said thiocarbonate salt comprises a tetrathiocarbonate.

30. The method defined in claim 25, wherein M is an alkaline earth metal, b is 3 or 4, or a value between 3 and 4, and y is 2.

31. The method defined in claim 25, wherein, in step (3), said thiocarbonate particles are dispersed in a water-resistance wax.

* * * * *